(12) United States Patent
Shalvi

(10) Patent No.: US 11,850,337 B2
(45) Date of Patent: Dec. 26, 2023

(54) AIR PURIFIER HAVING ULTRAVIOLET DISINFECTION MEANS

(71) Applicant: OLYMPIA LIGHTING, INC., Northvale, NJ (US)

(72) Inventor: Ram Shalvi, Closter, NJ (US)

(*) Notice: Subject to any disclaimer, the term of this patent is extended or adjusted under 35 U.S.C. 154(b) by 0 days.

(21) Appl. No.: 17/522,137

(22) Filed: Nov. 9, 2021

(65) Prior Publication Data
US 2022/0125986 A1    Apr. 28, 2022

Related U.S. Application Data

(63) Continuation of application No. 17/357,100, filed on Jun. 24, 2021, now Pat. No. 11,167,057.

(60) Provisional application No. 63/045,069, filed on Jun. 27, 2020.

(51) Int. Cl.
A61L 9/20      (2006.01)
B01D 46/00     (2022.01)
B01D 46/44     (2006.01)
B01D 46/46     (2006.01)

(52) U.S. Cl.
CPC ............ *A61L 9/20* (2013.01); *B01D 46/0027* (2013.01); *B01D 46/0028* (2013.01); *B01D 46/0049* (2013.01); *B01D 46/444* (2013.01); *B01D 46/46* (2013.01); *A61L 2209/111* (2013.01); *A61L 2209/12* (2013.01); *A61L 2209/14* (2013.01); *B01D 2273/30* (2013.01); *B01D 2279/65* (2013.01)

(58) Field of Classification Search
CPC ... A61L 9/20; B01D 46/0027; B01D 46/0028; B01D 46/0049; B01D 46/444; B01D 46/46
See application file for complete search history.

(56) References Cited

U.S. PATENT DOCUMENTS

2005/0000365 A1* 1/2005 Nelsen ...................... A61L 9/20
96/224

* cited by examiner

*Primary Examiner* — Robert A Hopkins
(74) *Attorney, Agent, or Firm* — Law Offices of Albert Wai-Kit Chan, PLLC; Robert D. Katz, Esq.

(57) ABSTRACT

The present invention provides an air purifier that purifies, disinfect and decontaminate convention air flow by using UV rays. Because the UV rays emitted by the UV light sources are contained within the air purifier, use of the air purifier is safe in that a nearby person can avoid exposure to hazardous UV radiation. Adjustment of operating conditions, such as the UV intensity and wavelength and air speed, is programmable via a remote controller, a smart switch, a smart device, a wireless communication device, a smart home control appliance, a sensing device, and/or a built-in module, which renders the air purifier a smart appliance that may automatically and optimally suits to a user's need based on the user's habit and other physical parameters. Installation and removal of the air purifier, as well as cleaning and replacement of any part thereof, are simple and convenient, as a result of the clever design.

15 Claims, 6 Drawing Sheets

AIR PURIFIER HAVING ULTRAVIOLET DISINFECTION MEANS

CROSS-REFERENCE TO RELATED APPLICATION

This application is a Continuation of U.S. Ser. No. 17/357,100, filed Jun. 24, 2021, which claims the benefits of U.S. Ser. No. 63/045,069, filed Jun. 27, 2020. The entire contents and disclosures of the prior application are incorporated herein by reference into this application.

Throughout this application, various references are referred to and disclosures of these publications in their entireties are hereby incorporated by reference into this application to more fully describe the state of the art to which this invention pertains.

FIELD OF THE INVENTION

The present invention relates to air purifiers that include disinfection and/or decontamination by ultraviolet (UV) radiation.

BACKGROUND OF THE INVENTION

Ultraviolet radiation can be utilized for germicidal disinfection and decontamination of air and surfaces. UV radiation is the electromagnetic radiation that falls in the region of spectrum between visible light and x-rays. UV radiation is invisible to the human eye and includes wavelengths in the spectral range of 100 to 400 nanometers (nm). This spectral range can be subdivided into four regions: vacuum UV rays with wavelengths in the range of 100 to 200 nm, UVC rays with wavelengths that range from 200 to 280 nm, UVB rays with wavelengths that range from 280 to 315 nm, and UVA rays with wavelengths that range from 315 nm to 400 nm. Because of the spectral sensitivity of the DNA and RNA in bacteria and viruses, only the UVC region demonstrates significant germicidal properties. According to the 2006 U.S. EPA UV Disinfection Guidance Manual (1), recommended UVC exposure dosage, which is measured as the product of UVC light intensity multiplied by exposure time, should be at least 2,500 µW·s/cm$^2$ and up to 8,000 µW·s/cm$^2$ for effectively killing 90% of most bacteria and viruses.

Conventional devices using UV radiation for disinfection and/or decontamination, such as low-pressure UV lights and/or UV lamps, may present problems with safety and effectiveness. Extensive and prolonged exposure to UV radiation may be associated with occurrence of skin cancers and may also cause health problems to the eyes. The effectiveness index of a conventional UV lamp is typically around 80%, which does not put the UVC region to most effective use. The present invention addresses the foregoing issues with innovative designs and optimal spectral tuning.

SUMMARY OF THE INVENTION

The present invention provides an air purification system comprising a multi-piece rigid housing having a detachable inlet for receiving air, a detachable outlet for exhausting air, and one or more utility openings, wherein a stream of air is passable from the inlet to the outlet; a UV light subsystem fitting the outlet and comprising a plurality of UV light sources that are configured to emit UV radiation with adjustable wavelengths to irradiate a stream of air in the interior of the air purification system; an air convection means configured to continuously move a stream of air (a) through the inlet from outside into the interior of the air purification system, (b) within the air purification system, from the inlet towards the outlet, and (c) through the outlet, from the interior to outside the air purification system; an air filtration means fitting the inlet and configured to remove particulates from a stream of air; an operation control subsystem having a plurality of control functions and configured to control the air purification system's operating status including the status of the air purification system and the status of any component of the air purification system, wherein the UV light subsystem, the air convection means, the air filtration means, and the operation control subsystem are enclosed by the housing; the operation control subsystem is adapted to the utility openings, through which an operator of the air purification system can access the control functions; when the air purification system is operating, a stream of air moved by the air convection means enters the interior of the air purification system, is irradiated by the UV light sources and filtered by the air filtration means, and exits the air purification system via the outlet, thereby being purified, disinfected and decontaminated by the air purification system.

The air purification system of the present invention may further comprise a UV sensor and motion sensors such as High Frequency Doppler (HFD) sensors inside the housing.

In one embodiment, the UV radiation emitted by the UV LED light sources is in the wavelength range of 200 nm to 400 nm. In one embodiment, the UV radiation emitted by the UV LED light sources is in the wavelength range of 240 nm to 290 nm. In another embodiment, the UV radiation emitted by the UV LED light sources has peak wavelength range of 260 nm to 270 nm. In one embodiment, the UV radiation emitted by the UV LED light sources has a wavelength of approximately 405 nm, which is both visible to the human eye and effective for bacterial decontamination. In one embodiment, the UV radiation emitted by the UV LED light sources break down and inactivate infectious organisms such as bacteria, viruses, and other pathogens, and thereby disinfects and decontaminates air and surrounding surfaces.

DETAILED DESCRIPTION OF THE INVENTION

Figure 1:
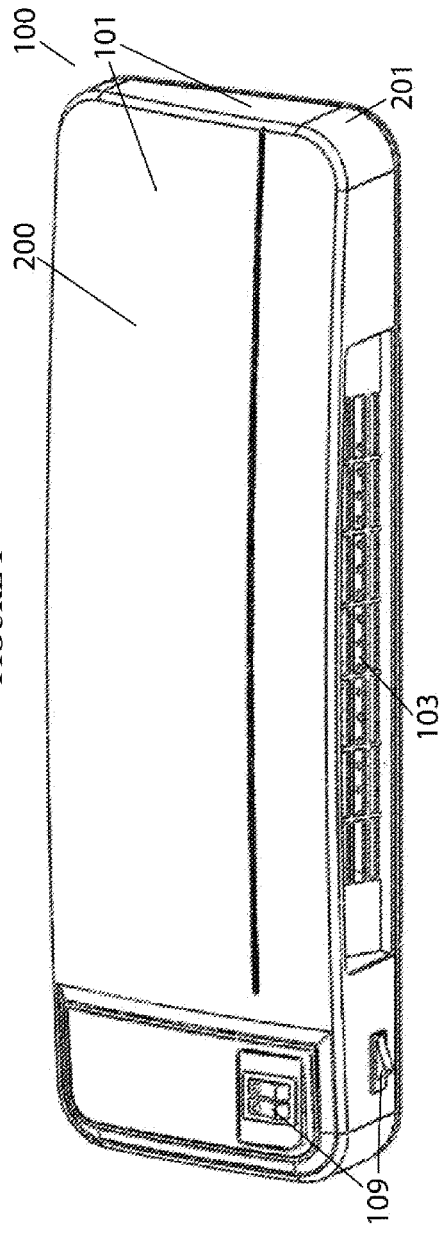
FIG. 1 is a front perspective view of the air purification system in accordance with the present invention.
Figure 2:
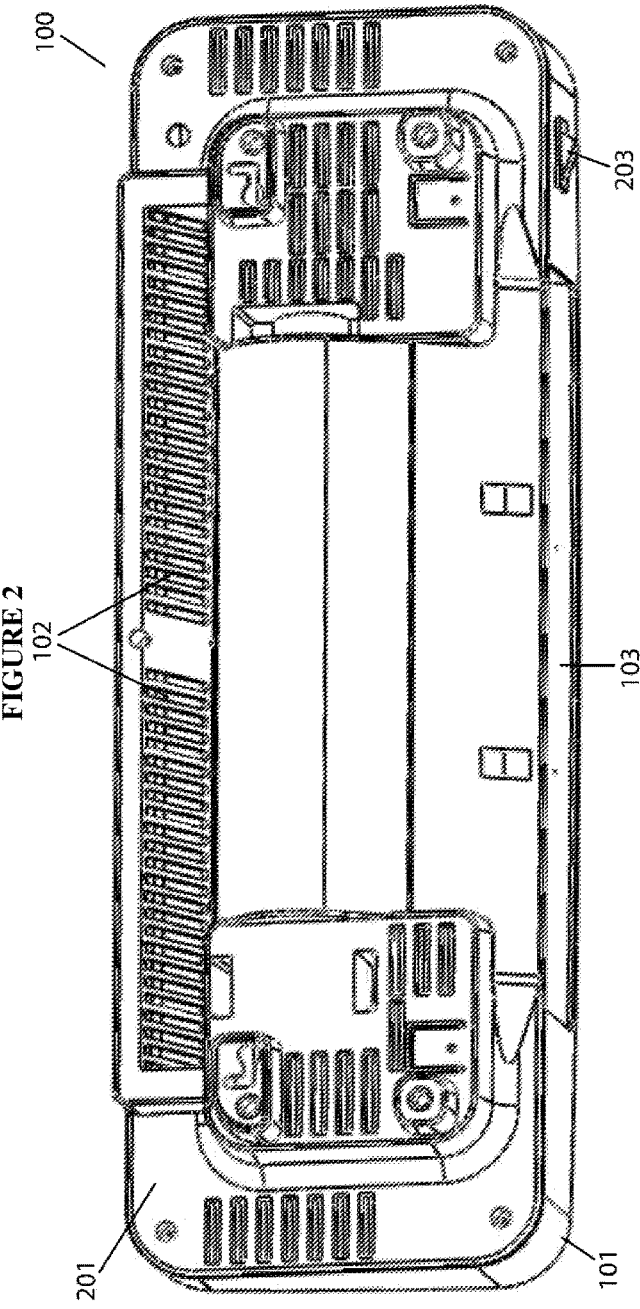
FIG. 2 is a rear perspective view of the air purification system in accordance with the present invention.

The present invention provides an air purification system (100) comprising a multi-piece rigid housing (101) having a detachable inlet (102) for receiving air, a detachable outlet (103) for exhausting, and one or more utility openings (104), wherein a stream of air is passable from the inlet (102) to the outlet (103); a UV light subsystem (105) fitting the outlet (103) and comprising a plurality of UV light sources (106) that are configured to emit UV radiation with adjustable wavelengths to irradiate a stream of air in the interior of the air purification system (100); an air convection means (107) configured to continuously move a stream of air (a) through the inlet (102) from outside into the interior of the air purification system (100), (b) within the air purification system (100), from the inlet (102) towards the outlet (103), and (c) through the outlet (103), from the interior to outside the air purification system (100); an air filtration means (108) adjacent to the inlet (102) and configured to remove particulates from a stream of air; an operation control subsystem (109) having a plurality of control functions and configured to control the air purification system's (100) operating status including the status of the air purification system (100) and the status of any component of the air purification system (100), wherein the UV light subsystem (105), the air convection means (107), the air filtration means (108), and the operation control subsystem (109) are enclosed by the housing (101); the operation control subsystem (109) is adapted to the utility openings (104), through which a user of the air purification system (100) can access the control functions; when the air purification system (100) is operating, a stream of air moved by the air convection means (107) enters the interior of the air purification system (100), is irradiated by the UV light sources (106), filtered by the air filtration means (108), and exits the air purification system (100) via the outlet (103), thereby being purified, disinfected and decontaminated by the air purification system (100).

The air purification system (100) of the present invention may further comprise a UV sensor and motion sensors such as High Frequency Doppler (HFD) sensors inside the housing (101).

The following terms shall be used to describe the present invention. In the absence of a specific definition set forth herein, the terms used to describe the present invention shall be given their common meaning as understood by those of ordinary skill in the art.

Figure 3:
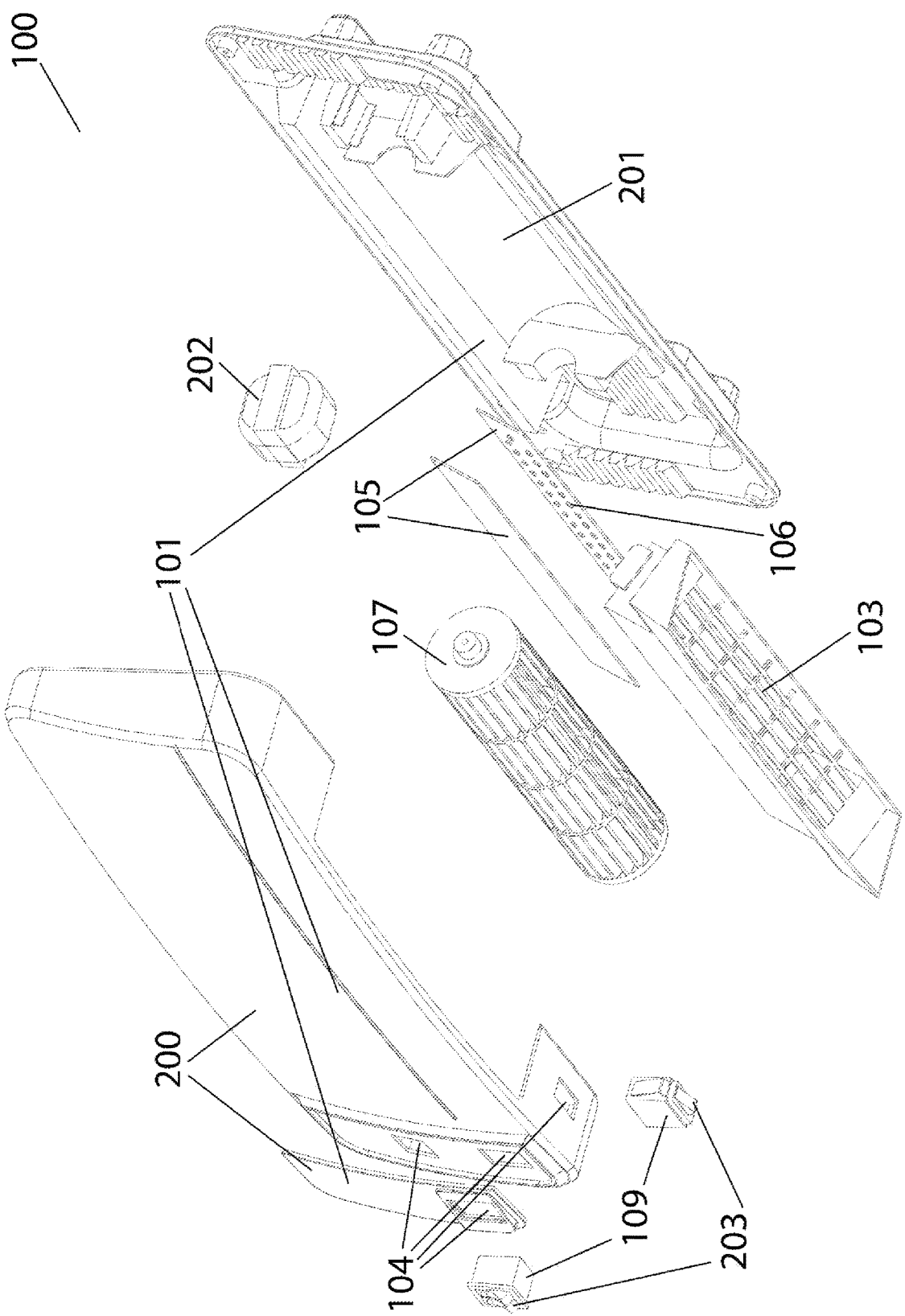
FIG. 3 is an exploded view of the air purification system in accordance with the present invention.
Figure 4:
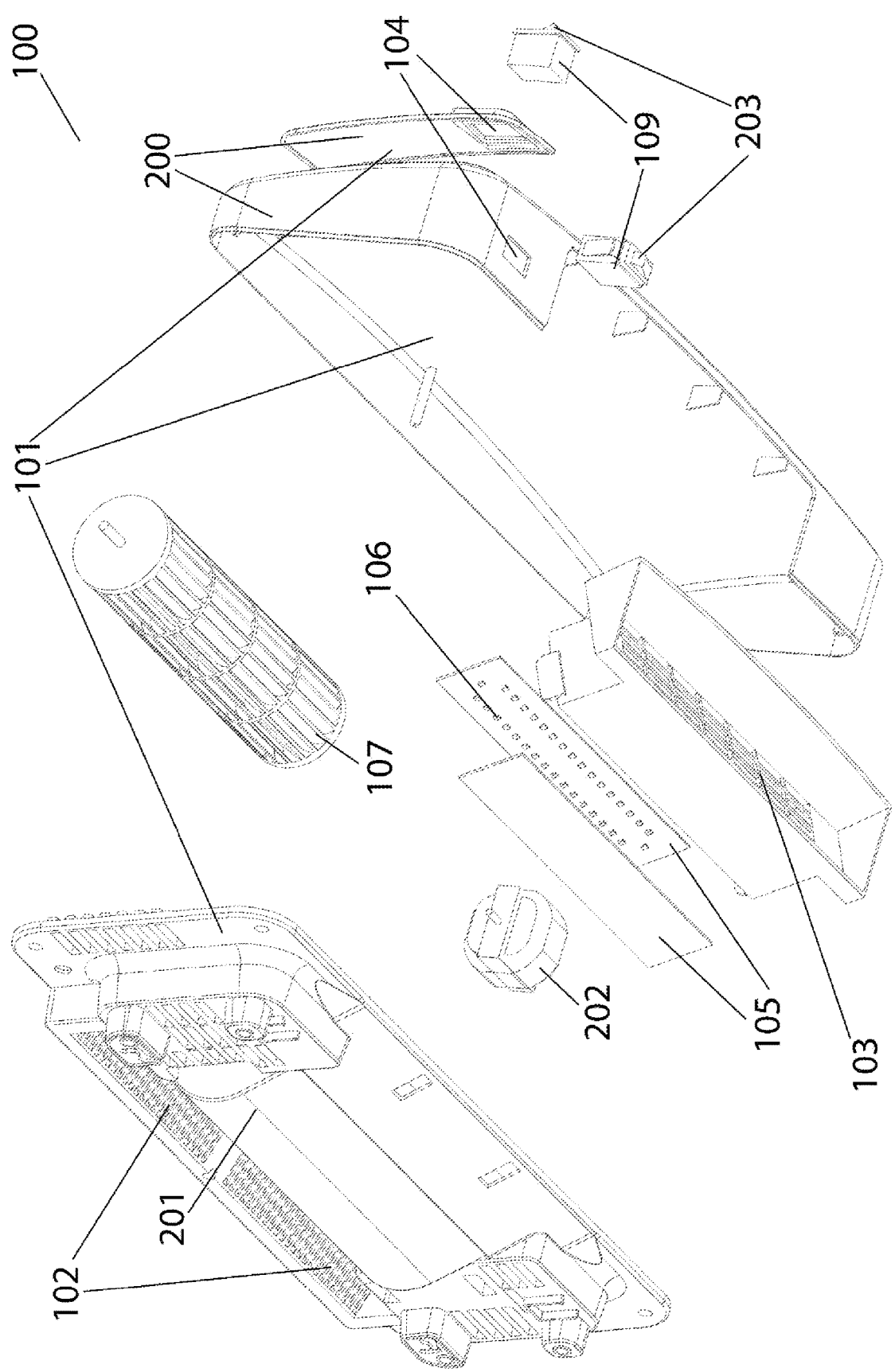
FIG. 4 is an exploded perspective view of the air purification system in accordance with the present invention.

The housing (101) is an enclosure protecting internal components, such as the UV light subsystem (105), the air convection means (107), the air filtration means (108), and the operation control subsystem (109). In one embodiment, the housing (101) is made of metal, plastic, and/or other materials, depending on actual needs in practice and use. In one embodiment, the housing (101) is manufactured in several constituent pieces that are assembled together to form the entire housing (101). As illustrated in FIGS. 3 and 4, the inlet (102) and the outlet (103) are, for example, two of the constituent pieces and are embedded in the housing (101). In one embodiment, the housing (101) includes a front section (200) and a rear section (201), with the inlet (102) embedded on the top of the rear section (201) and the outlet (103) embedded at the bottom of the front section (200), although the location of the inlet (102) and the outlet (103) may be arranged differently in accordance with design preference. The housing (101) has one or more utility openings (104) that fit signal receivers, control panels/interfaces, and/or switches for the internal operation control subsystem (109), to allow a user's access to the control functions. In one embodiment, the housing (101) is designed to feature mounting holes on the surface of the housing (101), which facilitate easy installation onto and removal from a wall or ceiling.

The inlet (102) is a set of slits detachably embedded in the housing (101) and allows air to enter from outside into the interior of the air purification system (100). The slit width and spacing can vary, depending on actual needs in practice and use.

The outlet (103) is a set of slits detachably embedded in the housing (101) and allows air to exhaust from the interior to outside the air purification system (100). The slit width and spacing can vary, depending on actual needs in practice and use. A disinfection chamber is defined as the space occupied by a stream of air from the air convection means (107) to the outlet (103), where UV disinfection of the stream of air occurs.

Figure 5:
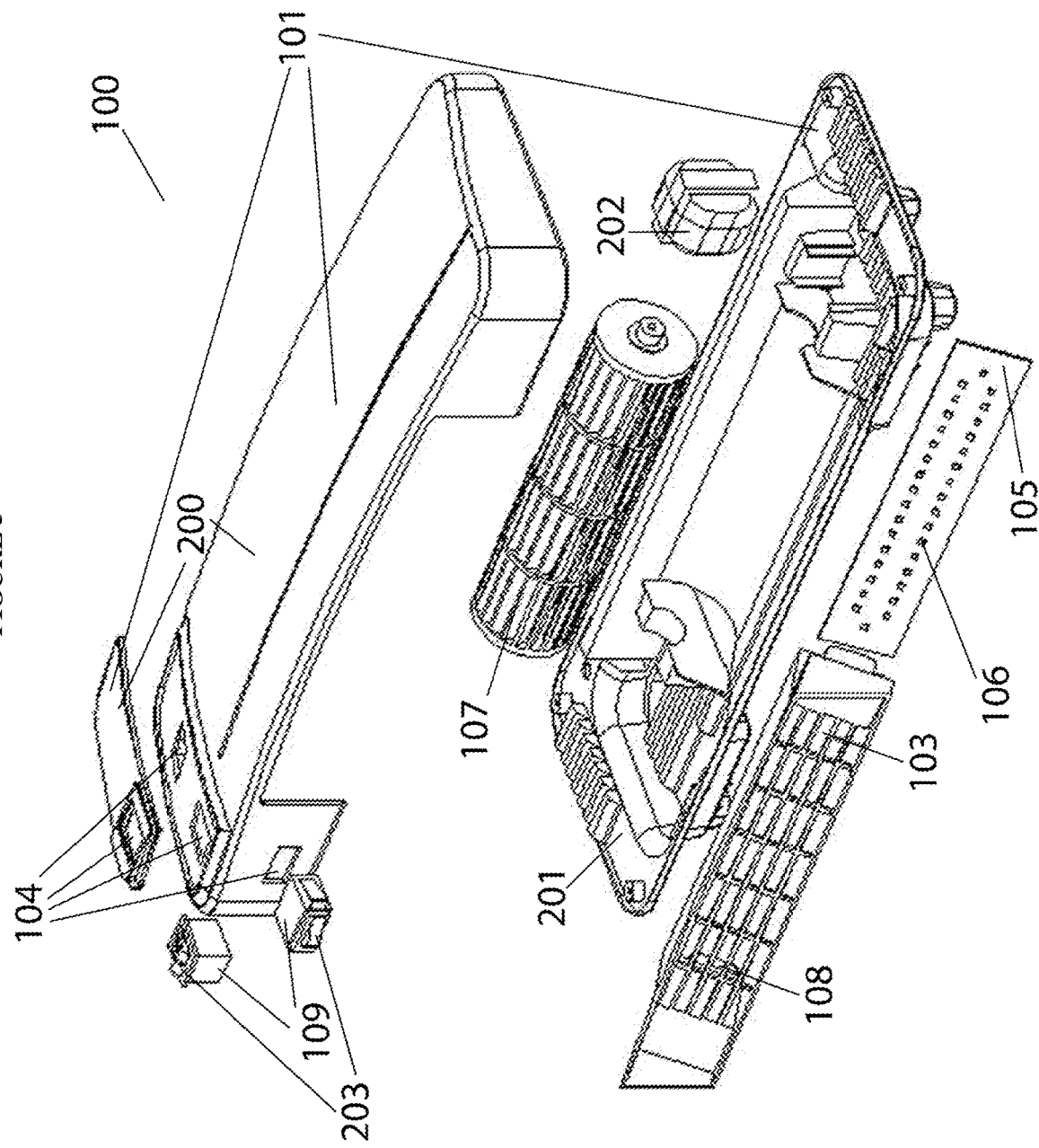
FIG. 5 is an exploded perspective view of the air purification system in accordance with the present invention.
Figure 6:
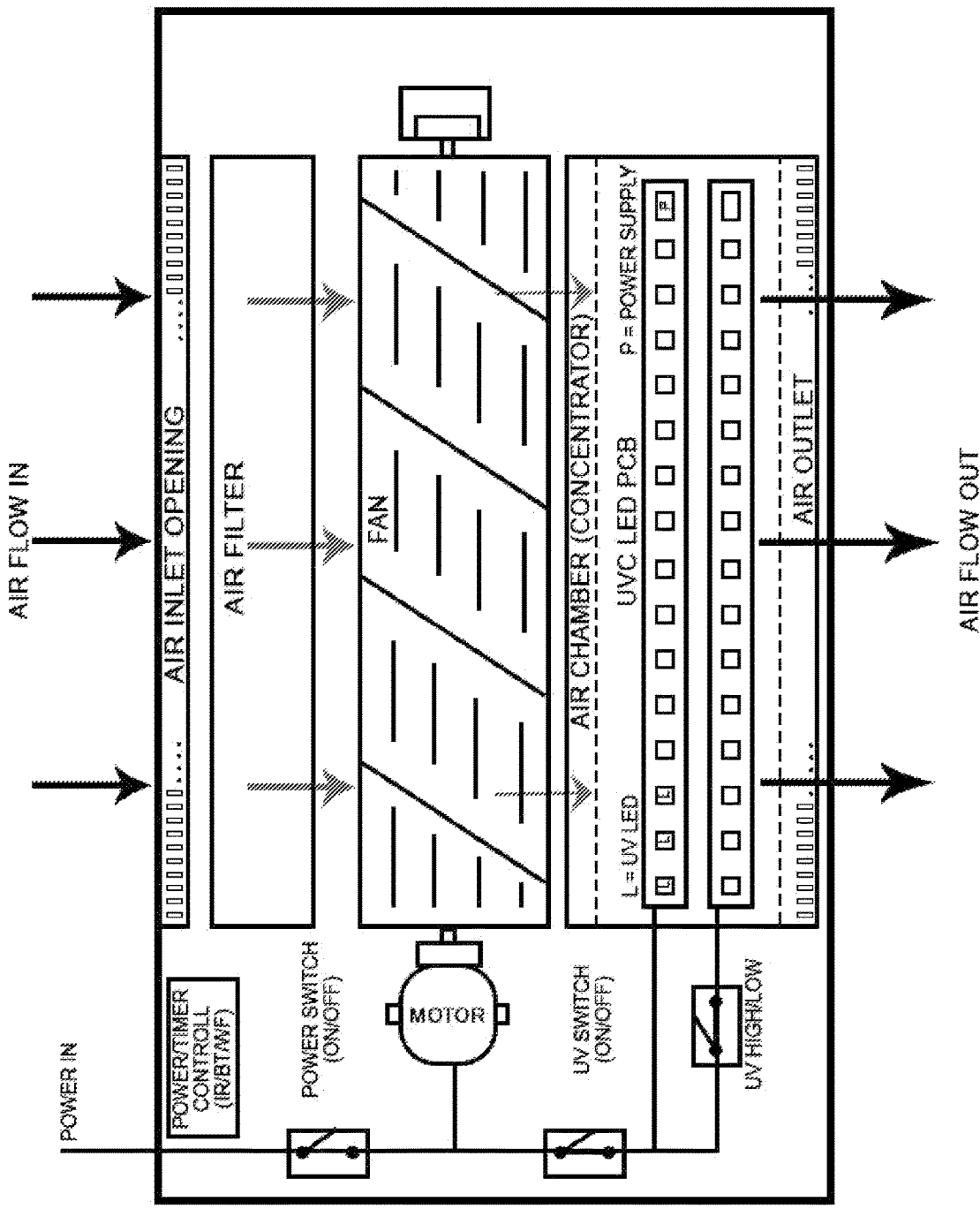
FIG. 6 is a flow diagram illustrating a stream of air passing through the air purification system in accordance with the present invention.

The utility openings (104) may be carve-outs that are designed and manufactured in the housing (101) or on the constituent pieces thereof. As illustrated in FIG. 5, the utility openings (104) are configured and adapted to fit various panels, interfaces and/or switches of the operation control subsystem (109). Location and dimension of each of the utility openings (104) can be adjusted during the manufacturing process, depending on actual needs in practice and use.

The UV light subsystem (105) comprises UV light sources (106) that are assembled on a UV light substrate, and any circuitry for electrical power and control thereof. In one embodiment, the UV light substrate is a printed circuit board (PCB) onto which UV LEDs (106) are soldered together with an electronic component for controlling the UV LEDs (106).

Aluminum has excellent thermal conductivity. In one embodiment, the UV light substrate is a PCB, and its main ingredient comprises aluminum for optimal heat dissipation. Heat generated by the UV light sources (106) can quickly be transferred to the aluminum PCB, and further to the convention air exhausted through the outlet (103), so that the operating temperature of the UV light sources (106) is maintained at a level that prolongs their longevity. In one embodiment, the aluminum PCB prevents the UV LED light sources (106) from overheating and maintains their operating temperature within a specified normal range during extensive use.

In one embodiment, the UV light sources (106) are UV LEDs soldered on one or more PCBs, and the PCBs are mounted within the disinfection chamber and next to the outlet (103), such that a stream of air is irradiated by the UV rays emitted by the UV LEDs (106) before it is exhausted through the outlet (103). The PCBs are rectangle in shape, and the UV LEDs (106) are arranged in a regular grid pattern with fixed spacing along the length and width of the PCBs. An integrated circuit chip, i.e., the electronic component, is also soldered on each of the PCBs to convert commercial power into a power supply for the UV LEDs (106). The integrated circuit chips receive control commands from the operation control subsystem (109). The integrated circuit chips are directly connected to the UV LEDs (106) and control the On/Off states, intensity and wavelengths of the UV LEDs (106).

The UV light sources (106) are chosen to emit desired optical wavelengths in the ultraviolet spectrum. The UV light sources (106) are enclosed inside the air purification system (100) by the housing (101) and arranged in a predetermined pattern (e.g., strip, panel, lattice grid, etc.) that is desired in practice and use, usually with a fixed spacing for uniform illumination. When powered on, the UV light sources (106) emit UV light that projects outwards, irradiates the interior of the air purification system (100), and disinfects and/or decontaminates air passing through the system to cleanse the surrounding area. In one embodiment, the UV light sources (106) are ultraviolet light-emitting diodes (UV LEDs) including LEDs for emitting UVC rays (e.g., UVC LEDs with a spectrum of wavelengths centered at approximately 265 nm) and near UVA rays (e.g., Near UVA LEDs with a wavelength of approximately 405 nm). In one embodiment, the UV light sources (106) are UV LEDs, and each UV LED comprises two or more LED chips combined into a single LED component, such that each UV LED emits both UVC rays with a center wavelength of approximately 265 nm and near UVA rays with a wavelength of approximately 405 nm simultaneously. In one embodiment, the UV light sources (106) comprise UVC LEDs and Near UVA LEDs that are assembled, e.g., soldered, onto one or more PCBs in any desired combination that depends on actual needs in practice and use, wherein the UVC LEDs emit UVC rays with a center wavelength of approximately 265 nm, and the Near UVA LEDs emit near UVA rays with a wavelength of approximately 405 nm, allowing flexibility in the selection and/or manipulation of a desired spectrum of wavelengths.

Existing technology for air disinfection by UV radiation, such as conventional UV lamps and UV lights, often resorts to ultraviolet quartz sleeves and tubes powered by external ballasts as the source of UV rays. Compared to the present invention using UV LEDs (e.g., UVC LEDs and Near UVA LEDs) (106), the existing technology has disadvantages due to larger dimension of the UV sleeves, fewer choices of the sleeve shape, more overheating, shorter life span, and the like, so available designs are less flexible and limited. The present invention adopts UV LEDs (106) which are much smaller in volume, generate less heat in operation, and last longer in use. The UV LEDs (106) may be assembled alongside the integrated circuit chip onto one PCB assembly that is the core of the UV light subsystem (105). As a single component, the UV light subsystem (105) can be as small, light-weight and compact as possible to open up possibilities for innovative designs and attractive shapes of the air purification system (100).

The UV light sources (106) can be arranged and assembled on panels, such as on UV light substrates. In one embodiment, one UV light substrate comprising a number of UV LEDs (106) is placed near the outlet (103), such that the UV rays emitted by the UV LEDs (106) may irradiate the stream of air when it is exhausted through the outlet (103). Using only one UV light substrate reduces cost of energy. In another embodiment, two UV light substrates, each comprising a number of UV LEDs (106), are placed in parallel near the outlet (103), such that the stream of air is sandwiched in between the substrates and is irradiated by the UV rays emitted by the UV LEDs (106). Using two or more substrates of UV LEDs (106) leads to quick and effective air disinfection.

In one embodiment, the UV light sources (106) are UV LEDs (106) that have a rated life of up to 30,000 to 50,000 hours (measured as the time of use after which the UV LEDs optical output decreases to 70% of the original value), which is about 2.5 to 5 times superior to that of typical quartz tubes. In comparison, the rated life of quartz tubes is typically under 12,000 hours.

The brightness, effectiveness and longevity of UV LEDs (106) are inversely proportional to their operating temperature. In one embodiment, the lifetime or longevity of the UV LEDs (106), can be increased by using a large number of such UV LEDs (106) operating at an electrical power lower than the nominal power output, so as to reduce the produced heat and maintain the UV light subsystem (105) at an operating temperature that prevents overheating. In one embodiment, the lifetime or longevity of the UV LEDs (106), is increased to 200% of their rated life, by operating at an electrical power equal to 50% of their nominal power.

In one embodiment, the air purification system (100) further comprises a UVC sensor near the UV light subsystem (105) inside the housing (101), for detecting the intensity of UVC rays emitted by the UV light sources (106) in the interior of the air purification system (100). In one embodiment, based on sensory data received from the UVC sensor, the air purification system (100) automatically modulates the electric power supplied to the UV light sources (106) so as to maintain a constant level of UVC intensity in the interior of the air purification system (100). In one embodiment, the electrical power supplied to brand-new UV light sources (106) is 70% of the nominal power supply of the UV light sources (106), and, after use for a period time and when the UVC sensor detects a 10% reduction of the intensity of UVC rays in the interior of the air purification system (100), the air purification system (100) automatically modulates the electrical power supplied to the UV light sources (106) to 80% of their nominal power supply. In one embodiment, by modulating the electrical power supplied to the UV light sources (106), the longevity of the UV light sources (106) can be increased, and the UVC intensity is maintained at a constant level during the use of the air purification system (100).

In one embodiment, the UV light sources (106) have peak wavelengths in the range of approximately 265 nm for optimal disinfection and decontamination. In one embodiment, the UV light sources (e.g., UV and/or UVC LEDs) (106) have peak wavelengths in the range of 260 to 270 nm and total optical power output of at least 60 to 80 mW when operating at 500 mA.

In one embodiment, while emitting UVC rays, the UV light sources (106) further comprise UVA LEDs (106) configured to emit near UVA rays at an approximate wavelength of 405 nm. Near UVA rays at a wavelength of approximately 405 nm are visible to the human eye, and their bactericidal effects, i.e., inactivation of bacteria such as *Escherichia, Salmonella, Shigella, Listeria*, and *Mycobacterium* species are demonstrated by a previous study (2).

Conventional UV disinfection systems rely on UVC radiation at a wavelength of approximately 254 nm and may only achieve a Peak Germicidal Disinfection Effectiveness (PGDE) Index of approximately 80%. Compared to those conventional systems, the air purification system (100) of the present invention optimally tunes the wavelength of UVC radiation in the range of 250 to 300 nm to a peak wavelength of approximately 265 nm, so that it can achieve a PGDE Index of almost 100%.

In one embodiment, the UV light sources (106) are UV LEDs, and each UV LED may attain a viewing angle of 130 degrees, a forward voltage between 5.0 and 9.0 V when operating at 500 mA, a junction-to-case thermal resistance of 7.0° C./W, and a power dissipation of 4.0 W or no greater than 4.5 W when operating at 500 mA.

In one embodiment, the UV light sources (106) can tolerate a continuous forward current of 100 to 700 mA or of 500 mA, a reverse voltage of no higher than about 5 V, a case temperature in the range of −10 to 80° C. when operating at 500 mA, a storage temperature of −40 to 100° C., and a junction temperature no higher than 115° C.

In one embodiment, the UV light sources (106) have preheat or soak temperature between limit temperatures of 150° C. ($T_{smin}$) and 200° C. ($T_{smax}$), and time for transition between the limit temperatures is 60 to 120 seconds. The UV light sources (106) have a liquidus temperature ($T_L$) of approximately 217° C., a maximum peak package body temperature ($T_P$) of 260° C., a maximum ramp-up rate of 3° C./s, and a time maintained above $T_L$ of 60 to 150 seconds ($t_L$). The UV light sources (106) have a maximum ramp-down rate of 6° C./s from $T_P$ to $T_L$ and a maximum time of approximately 8 minutes from 25° C. to $T_P$.

In one embodiment, the UV light sources (106) have a power of 30 to 150 W, a flux of 10 to 10,000 µW/cm² so as to achieve a UVC exposure dosage of at least 2,500 µW·s/cm² in the interior of the air purification system (100) within several seconds to several minutes of use, and an irradiation of 200 to 3,000 mW which is a high UV intensity for fast and effective disinfection and decontamination of an airstream as discussed below.

Compared to conventional UV disinfection systems, the air purification system (100) of the present invention provides safety protection of a person nearby from UV hazard, such as protecting a nearby person's eye health, by a clever design that contains the UV light sources (106) and UV rays emitted thereby within the enclosure. Exposure to UV radiation can be dangerous and associated with damage to eyesight and incidence of skin cancers, and a person adjacent to UV systems should be protected from direct exposure of UV radiation. When operating and emitting UVC radiation, the air purification system (100) of the present invention prevents the UV rays from propagating outside the air purification system (100) to avoid exposing a nearby person to the UV radiation. Since UV rays inside the air purification system (100) are invisible to the person nearby, safety of use of the air purification system (100) is enhanced. The Near UVA rays emitted by the Near UVA LEDs (106) are an indicator and deterrent, and they serve as a safety measure when a user intentionally or accidentally opens the housing (101) during the air purification system's (100) operation. Observing the near UVA rays, the user, or a nearby person, can be alerted and turn off the UV rays to avoid extensive exposure.

UV rays emitted by the UV light sources (106) in the present invention irradiate only the interior of the air purification system (100) and do not spread into space outside the air purification system (100), so a person near the air purification system (100) is protected against unsafe UV radiation. In one embodiment of the present invention, when the air purification system (100) is operating, UV rays cannot be detected in the outside space in proximity to the air purification system (100). In one embodiment of the present invention, when the air purification system (100) is operating, UV rays detected in the proximity of the air purification system (100) are less than 0.1% of the total optical power of the UV light sources (106), i.e., less than 0.1 µW/cm², corresponding to an absolute safe level for extensive use by human.

The air convection means (107) moves air to flow through the inlet (102) and outlet (103) on the housing (101) and within the interior of the air purification system (100). When operating, the air convection means (107) generates an air pressure ingredient that causes air to enter through the inlet (102) on the housing (101) into the interior of the air purification system (100), pass within the air purification system (100) from the inlet (102) towards the outlet (103), and exits the air purification system (100) through the outlet (103) on the housing (101). With the air convection means (107), a stream of air is drawn from the surrounding space and circulated through the air purification system (100) for purification, disinfection and decontamination, before it exits and returns to surrounding space. The air convection means (107) has an adjustable operating power, so that it may run at a low speed, a high speed, or any other speed between the two. A low or comfortably negligible noise is rendered at the low speed, and a high throughput of air stream is enabled at the high speed, so that the air purification system (100) is suited for use in a large space despite its seemingly small form factor. In one embodiment, the air convection means (107) has a flow rate of up to 50 to 100 cu. ft. per minute, i.e., 50 to 100 CFM, when operating at the high speed. In one embodiment, the air convection means (107) has a flow rate of up to 200 CFM at the high speed, suiting space of up to 800 sq. ft. In one embodiment, the air convection means (107) has a flow rate of up to 350 CFM at the high speed, suiting space of up to 1,200 sq. ft. In one embodiment, the air convection means (107) has a flow rate of up to 400 CFM at the high speed, advantageous for use in space with high ceiling and/or larger area than 1,200 sq. ft. The air convection means (107) is detachably assembled into the housing (101), facilitating replacement when needed.

In one embodiment, the air convection means (107) is a centrifugal pump impeller whose rotation is driven by an AC or DC electric motor (202). In one embodiment, the impeller has 3 to 5 vanes. In another embodiment, the impeller has 7 or more vanes. In one embodiment, the impeller and its driving motor (202) are mounted on an internal mount structure inside the housing (101), wherein the mount structure is rigidly attached to the inner surface of the housing (101), such as the inner surface of a rear section (201).

In one embodiment, the air convection means (107) is a fan that is propelled by a small AC or DC electric motor (202). The fan may have 4 to 8 blades. In one embodiment, the air convection means (107) may comprise two fans, one facing the inlet (102) and the other facing the outlet (103), which operate at the same time for an increased air flow.

In one embodiment, the air convection means (107) allows adjustment of operating power between 2 speeds, a high speed for high air flow throughput, and a low speed for comfortably negligible noise. In one embodiment, the air convection means (107) allows adjustment of operating power among 3 to 5 speeds, wherein the lowest speed renders comfortably negligible noise, and wherein the air purification system (100) can suit a large space up to 800 sq. ft. at the highest speed. In one embodiment, several air purification systems (100) of the present invention may cooperate at the high speed of the air convection means (107) at the same time, so as to accommodate an indoor space of any size.

The air filtration means (108) has an identical or similar shape as the inlet (102) of the housing (101) and is detachably attached thereto for removal of particulates from the air stream. Efficiency of the air filtration means (108) is increased by running the air convection means (107) at a higher speed. The air filtration means (108) is replaceable, and its easy installation also facilitates regular replacement within a certain period for continuing effectiveness of air decontamination.

In one embodiment, as illustrated in FIG. 5, the air filtration means (108) is an air filter commonly available in home-use or commercial air purifiers. In one embodiment, the air filtration means (108) is one air filter attached to and facing the inlet (102) of the housing (101). In one embodiment, the air filtration means (108) is an HEPA air filter. In one embodiment, the air filtration means (108) is replaced every month. In one embodiment, the air filtration means (108) is replaced every 3 months. In one embodiment, the air filtration means (108) is replaced every 6 months, depending on operating conditions and filter type.

The operation control subsystem (109) is the central processing and control unit that receives control instructions and sends control commands accordingly. The control instructions can be received from one or more sources including:
- (a) a remote controller using infrared and/or radio frequency;
- (b) a smart switch directly connected to the air purification system (100), which is optionally equipped with digital display of the air purification system's (100) operating status;
- (c) a transmitting device using wireless communication such as Wi-Fi and/or Bluetooth technologies;
- (d) a smart home control appliance including a smart speaker wirelessly connected to the air purification system (100);
- (e) a sensing device directly or wirelessly connected to the air purification system (100); and
- (f) a programmable module of the air purification system (100).

Figure 7:
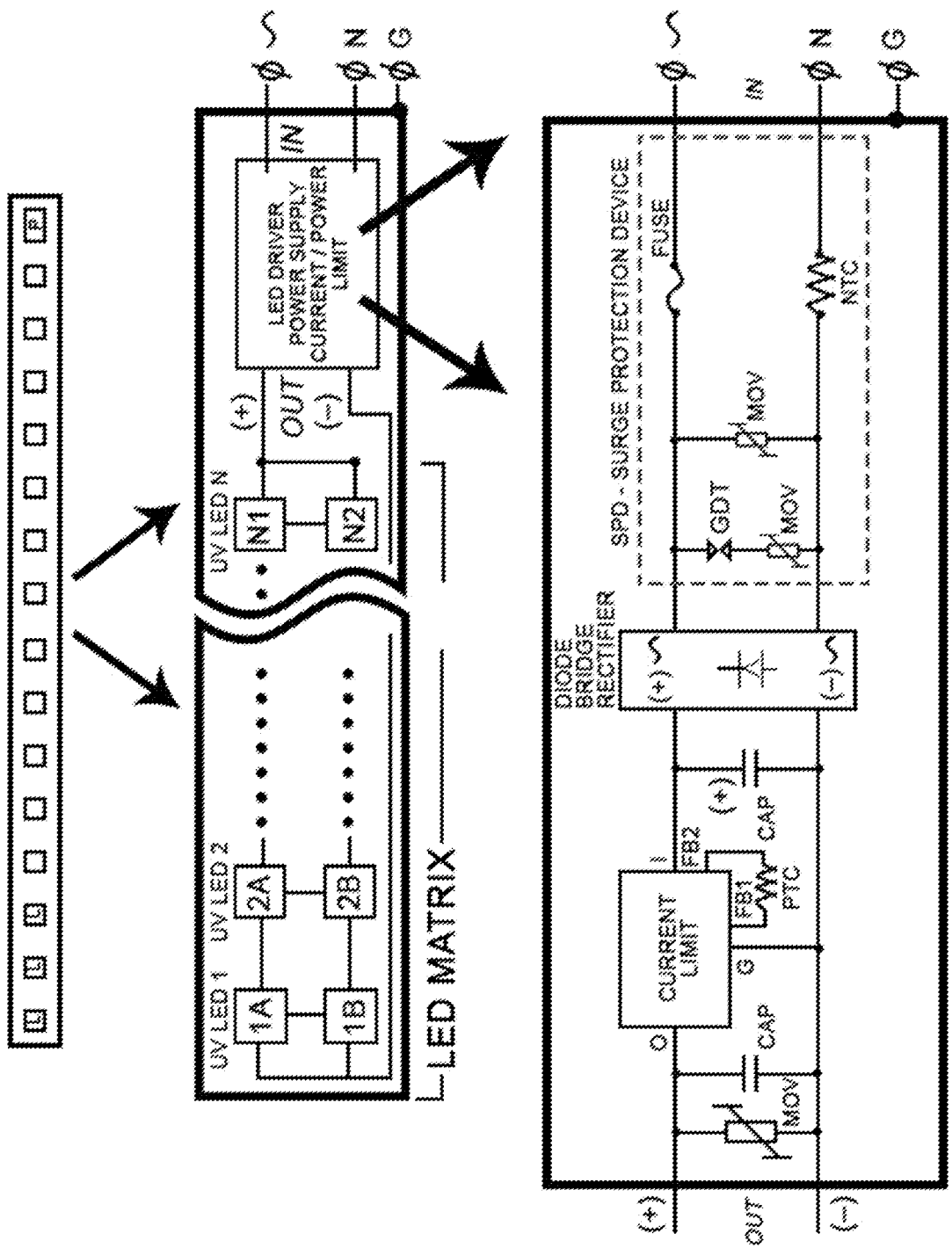
FIG. 7 is an electrical diagram illustrating the operating electrical connections of the air purification system in accordance with the present invention.

In one embodiment, the operator control system (109) comprises a driver, for example LED driver, which is an integrated circuit built into the air purification system (100) as illustrated in FIG. 7. The driver receives electric power from an outlet or other power sources, and it is configured to convert and modulate electric power of the UV light subsystem (105), the UV light sources (106), the air convection means (107), the AC or DC electric motor, or driving motor (202), the air filtration means (108), and the control box (203). The LED driver also supplies electric power to motion detection sensors and UV sensors, receives sensory signals from these sensors, and sends control commands to modulate operating conditions of the UV light sources (106) and the air convection means (107).

In one embodiment, the operation control subsystem (109) comprises a control box (203) fitting one of the utility openings (104) on the housing (101). A user can use the control box (203) to switch on or off the air purification system (100). When the air purification system (100) is switched on, the UV LEDs (106) light up and start emitting UV rays including UVC rays, and, driven by a motor (202), an impeller rotating at a predetermined speed draws air into the disinfection chamber to be irradiated by the UV LEDs (106) before it exists the air purification system (100) through the outlet (103). In one embodiment, the operation control subsystem (109) comprises multiple control boxes (203), each fitting one of the utility openings (104) on the housing (101) and controlling certain operating conditions or parameters of the air purification system (100).

The operation control subsystem (109) can power on or off the entire air purification system (100). Furthermore, by sending control commands, the operation control subsystem (109) can control the following operating status of the air purification system (100), including the operating conditions and parameters as follows:
- (a) On/Off state of the UV light subsystem (105);
- (b) Intensity of the UV rays emitted by the UV light sources (106);
- (c) Wavelength of the UV rays emitted by the UV light sources (106); and
- (d) Speed of the air convection means (107).

The air purification system (100) of the present invention may further comprise a motion sensor that is normally used in a surveillance apparatus such as a miniaturized security camera. In one embodiment, the air purification system (100) of the present invention comprises a High Frequency Doppler (HFD) sensor. Sensory signal of the motion sensor can be image-based, and the motion sensor can include a camera system that supports normal camera functionality such as capturing visual images. The sensory input can also be infrared ray-based, and the motion sensor can include a sensor unit with predetermined field of view. The sensory input can further be microwave-based, such as the HFD sensor, to achieve superior detection range and sensitivity.

In one embodiment, the air purification system (100) of the present invention comprises a motion sensor that transmits sensory signals indicating whether motion of a human is detected within a detection range, e.g., 3 to 12 meters. The detection range is tunable during manufacturing process and/or field adjustable via a switch or software. With a detection range up to 12 meters, the air purification system (100) can accommodate a large space with a high ceiling, such as hotel lobbies, large warehouses, or factories. In one embodiment, the air purification system (100) comprises a motion sensor with a maximum detection range of up to 12 meters. In one embodiment, the air purification system (100) comprises a motion sensor whose detection range can be field adjusted from 10% to 100% of the maximum detection range. In one embodiment, the air purification system (100) comprises a motion sensor whose detection range can be field adjusted to 10%, 30%, 50%, 75% or 100% of the maximum detection range.

In one embodiment, the motion sensor outputs one of two states as a control instruction, i.e., either motion of a human is detected (STATE 1) or is no longer detected (STATE 2) after a predetermined time period that is adjustable between 5 seconds and 30 minutes. To prevent false signals due to noises in surrounding environment, the motion sensor has a built-in sensitivity threshold, such that it only determines that a motion is detected (STATE 1), if the detection signal is above the threshold. The motion sensor sends an output of either STATE 1 or STATE 2 to the air purification system (100) which then adjusts operating conditions or parameters of the UV light subsystem (105) and the air convection means (107) independently.

In one embodiment, the motion sensor sends an output of STATE 1 as an instruction, when motion of a human is detected, and upon receiving the instruction, the operation control subsystem (109) sends control command to carry out one or more operations as follows:
- (a) powering the air purification system (100);
- (b) having the UV light sources (106) emit UVC rays;
- (c) having the UV light sources (106) emit near UVA rays at approximately 405 nm, e.g., by powering on the Near UVA LEDs (106) alone while keeping the UVC LEDs (106) off;
- (d) increasing the intensity of any of above UV light sources (106); and
- (e) increasing the speed of the air convection means (107).

Above operations may be carried out by the air purification system (100) independently.

In one embodiment, the motion sensor sends an output of STATE 2 as an instruction, when motion of a human is not detected for a predetermined time period that can be adjusted between 5 seconds and 30 minutes, and upon receiving the instruction, the air purification system (100) carries out one or more operations as follows:
- (a) powering off the Near UVA LEDs (106);
- (b) powering off the UVC LEDs (106);
- (c) decreasing the intensity of any of above UV light sources (106);
- (d) decreasing the speed of the air convection means (107);
- (e) powering off the air convection means (107); and (f) powering off the air purification system (100) entirely.

Above operations may be carried out by the air purification system (100) independently.

In one embodiment, upon receiving the STATE 1 or STATE 2 instruction, the operation control subsystem (109) automatically powers on or off the UV light subsystem (105) and the air convection means (107) simultaneously. In one embodiment, the UV light subsystem (105) remains powered on, regardless of the STATE 1 and/or STATE 2 instructions received by the operation control subsystem (109). In one embodiment, as a protection for people who are concerned with exposure to UV radiation, the operation control subsystem (109) automatically powers off the UV light subsystem (105) upon receiving a STATE 1 instruction, and powers the UV light subsystem (105) on upon receiving a STATE 2 instruction.

In one embodiment, the motion sensor sends an output of STATE 2 as an instruction, when motion of a human is not detected for a predetermined time period that can be field adjusted between 5 seconds and 30 minutes by a switch and/or software. In one embodiment, the motion sensor sends an output of STATE 2 as instruction, when motion of a human is not detected for a predetermined time period that can be field adjusted to 5 seconds, 30 seconds, 1 minute, 5 minutes, 10 minutes, 20 minutes and 30 minutes by a switch and/or software.

In one embodiment, the control command triggered by receipt of either the STATE 1 or STATE 2 instruction is programmable by a user on a remote controller, a smart switch, a smart device, a smart home control appliance, or software built into the operation control subsystem (109).

In one embodiment, the motion sensor sends an output of STATE 1 as an instruction, when motion of a human is detected, and upon receiving the instruction, the air purification system (100) automatically sets the air convection means (107) to operate at the high speed. In one embodiment, the motion sensor sends an output of STATE 2 as an instruction, when motion of a human is not detected for a predetermined time period, and upon receiving the instruction, the air purification system (100) automatically sets the air convection means (107) to a lower speed such as the low speed, or powers the air purification system (100) off.

By sending control commands based on received control actions, the operation control subsystem (109) offers the following control functions including:

(a) a "timer function" that powers on or off and adjusts any operating condition or parameter of the air purification system (100) at an adjustable preset time point or after an adjustable preset time elapse;

(b) an "UV intensity function" that adjusts the intensity of the UV rays emitted by the UV light sources (106);

(c) a "UV wavelength function" that adjusts the wavelength of the UV rays emitted by the UV light sources (106); and (d) an "air speed function" that adjusts the speed of the air convection means (107).

A use may access above functions via one or more above-mentioned sources sending control instructions to the air purification system (100).

In one embodiment, the air purification system (100) of the present invention provides a system for disinfection of air and surfaces through UVC irradiation that occurs with a line of sight between the UVC source and the air or the surface.

In one embodiment, the air purification system (100) provides surface and air disinfection for airborne viruses.

In one embodiment, air is propelled by the air convection means (107) and circulates through the air purification system (100), effectively reducing the operating temperature of the UV light subsystem (105) and the UV light sources (106), thus elongating the lifetime of the UV light sources (106).

In one embodiment, the air purification system (100) of the present invention can be instantly turned on or off. In one embodiment, the wavelength of the ultraviolet radiation emitted by the UV light sources (106) can be tuned from 250 nm to 285 nm.

In one embodiment, the UV light sources (106) achieves a longer lifetime of approximately 30,000 hours, which is superior to Quartz UV Tubes and Lamps that usually have lifetime of around 8,000 hours.

In one embodiment, the air purification system (100) monitors the internal airflow and modulates the intensity of UVC radiation as emitted by the UV light sources (106) to effectively deactivate microorganisms such as bacteria, viruses, and mold.

In one embodiment, the air purification system (100) has a built-in detector of internal airflow and automatic adjust the power of the UV light sources (106). In one embodiment, the air purification system (100) automatically increases the power of the UV light sources (106) when flow rate of the internal airflow is detected to be above a threshold.

In one embodiment, the air purification system (100) has a built-in wide voltage range LED driver operating from 100 to 480 Volts for quick and simple installation.

In one embodiment, the air purification system (100) further comprises magnets or clamps for mounts.

In one embodiment, the air purification system (100) comprises a UVC sensor or detector that sends a signal to the LED driver that provides power to the UVC LED light sources to maintain a constant level of UVC intensity in the interior of the air purification system (100).

In one embodiment, the air purification system (100) comprises an airflow sensor or detector that sends a signal to the LED driver that provides power to the UVC LED light sources to adjust the power of the UVC light sources.

In one embodiment, the interior of the air purification system (100) is partially or wholly made of aluminum, which has one or more reflecting surfaces for maximal reflection of UVC rays. In one embodiment, characteristics of the one or more reflecting surfaces are the same as or similar to those disclosed in WO 2017158989A1.

In one embodiment, the air purification system (100) of the present invention comprises a built-in surge protection, which protects the air purification system (100) from electrical surge during operation. In one embodiment, the surge protection device is integrated into the UV light subsystem (105) and/or the operation control subsystem (109).

In one embodiment, the air purification system (100) of the present invention may disinfect surfaces and air within a distance of 3 to 5 meters and achieve the almost 100% PGDE Index after a continuous use of 10 to 30 minutes.

In one embodiment, the air purification system (100) has one or more thermal sensors (thermistors) coupled to and/or integrated into the operation control subsystem (109), which sense the operating temperature of the UV light sources (106) and manages electric power to prevent overheating.

In one embodiment, the power of the UV light sources (106) is adjusted according to a predefined program to maintain a PGDE Index substantially in a range of 85% to 100%.

In one embodiment, the present invention provides an air purification system that comprises a housing having an inlet for receiving air, an outlet for exhausting air, and one or more utility openings, wherein an air stream is passable from the inlet to the outlet. The system also comprises an air convection means in the housing, which moves the air stream through the inlet from outside into a chamber in the housing, and further move the air stream from the chamber to outside through the outlet. The system further comprises a UV light subsystem within the chamber, comprising a plurality of UV light sources configured to emit UV radiation with adjustable wavelengths to irradiate the air stream passing through the chamber; and an operation control subsystem adapted to the utility openings on the housing, by which a user controls or adjusts the air convection means and UV light subsystem, wherein when the air purification system is in operation, the air stream moved by the air convection means enters the chamber through the inlet, is irradiated by the UV light sources of the UV light subsystem, and exits through the outlet, thereby being disinfected.

In one embodiment, the UV light subsystem comprises one or more PCBs for mounting the UV light sources in the chamber, wherein the PCBs comprise aluminum, so that heat accumulated in the chamber is efficiently dissipated, thereby lowering the operating temperature of the UV light sources and elongating the lifetime of the UV light sources.

In one embodiment, the UV light sources emit UVC rays with a wavelength ranging from 200 to 280 nm and UVA rays with a wavelength of approximately 405 nm, and wherein the UVA rays are visible to a bystander as a safety measure to signal UV leakage from the system.

In one embodiment, the UV light sources have a power of 30 to 150 W, a flux of 10 to 10,000 µW/cm2 so as to achieve an irradiation dosage of at least 2,500 µW·s/cm2 in the chamber within several seconds to several minutes of use, and an irradiation of 200 to 3,000 mW for rapid and substantially complete disinfection of the air stream.

In one embodiment, the air purification system further comprises an air filtration means attached to the air convection means, wherein the air filtration means removes particulates from the air stream before or after disinfecting the air stream.

In one embodiment, the air purification system further comprises a UVC sensor inside the chamber for detecting the intensity of UVC rays emitted by the UV light sources.

In one embodiment, based on sensory data received from the UVC sensor, the electric power supplied to the UV light sources is modulated to maintain a constant level of UVC intensity in the chamber.

In one embodiment, 70% of the nominal power supply is provided to new UV light sources while, when the UVC sensor detects a 10% reduction of the intensity of UVC rays in the chamber of the air purification system after use for a period time, the system increases power supplied to the UV light sources to 80% of their nominal power supply.

In one embodiment, the UV light sources with adjustable electric power have increased longevity.

In one embodiment, the UV light sources have a rated life of 30,000 to 50,000 hours, wherein the rated life is a period of time in which the UV light sources have an optical output of no less than 70% of the nominal power output.

In one embodiment, the air purification system achieves a PGDE Index in a range of 85% to 100%.

In one embodiment, the air purification system reduces COVID-19 virus in the air stream by 99.9%.

In one embodiment, operating conditions and parameters of the UV light sources and the air convection means are adjusted by a user via the operation control subsystem.

In one embodiment, the operation control subsystem intelligently adjusts the operating conditions and parameters based on instructions from the user saved on a smart home control appliance or encoded in a software operable with the operation control subsystem.

In one embodiment, the UV light sources in the chamber comprise two UVC LED strips facing one another to ensure the most potent irradiation and disinfection while minimizing UVC leakage from the air purification system.

In one embodiment, the air convection means comprises an airflow detector for detecting flow rate of air therein, wherein when the flow rate of air reaches a threshold value or a range, the airflow detector provides a signal to the operation control subsystem to adjust the power of the UV light sources.

In one embodiment, the power of the UV light sources is adjusted in a way to maintain a PGDE Index substantially in a range of 85% to 100%.

In one embodiment, the interior of the chamber has one or more reflecting surfaces made of aluminum for maximal reflection of UV rays.

In one embodiment, the air purification system further comprises a motion sensor for alarming a person adjacent to or present within a predetermined distance of the air purification system from possible exposure to the ultraviolet light emitted by the UV light sources due to UV light leakage.

In one embodiment, the motion sensor is a High Frequency Doppler (HFD) sensor.

Throughout this application, various references or publications are cited. Disclosures of these references or publications in their entireties are hereby incorporated by reference into the application in order to more fully describe the state of the art to which this invention pertains. It is to be noted that the transitional term "comprising", which is synonymous with "including", "containing" or "characterized by", is inclusive or open-ended, and does not exclude additional, un-recited elements or method steps.

REFERENCES

1. *Ultraviolet Disinfection Guidance Manual for the Final Long Term 2 Enhanced Surface Water Treatment Rule*. EPA 815-R-06-007. United States Environmental Protection Agency (November 2006).
2. Murdoch et al., *Bactericidal Effects of 405 nm Light Exposure Demonstrated by Inactivation of Escherichia, Salmonella, Shigella, Listeria, and Mycobacterium Species in Liquid Suspensions and on Exposed Surfaces*. Scientific World J. Vol 2012, Article ID 137802 (2012).

What is claimed is:

1. An air purification system, comprising:
   a housing having an inlet for receiving air, an outlet for exhausting air, and one or more utility openings, wherein an air stream is passable from the inlet to the outlet;
   an air convection means in the housing, which moves the air stream through the inlet from outside into a chamber in the housing, and further moves the air stream from the chamber to outside through the outlet;
   a UV light subsystem within the chamber, comprising a plurality of UV light sources configured to emit UV radiation with adjustable wavelengths to irradiate the air stream passing through the chamber; and an operation control subsystem adapted to the utility openings on the housing, by which a user controls or adjusts the air convection means and UV light subsystem, wherein when the air purification system is in operation, the air stream moved by the air convection means enters the chamber through the inlet, is irradiated by the UV light sources of the UV light subsystem, and exits through the outlet, thereby being disinfected, wherein the UV light subsystem comprises one or more PCBs for mounting the UV light sources in the chamber, wherein the PCBs comprise aluminum, so that heat accumulated in the chamber is efficiently dissipated, thereby lowering the operating temperature of the UV light sources and elongating the lifetime of the UV light sources, wherein the air purification system further comprises a UVC sensor inside the chamber for detecting the intensity of UVC rays emitted by the UV light sources.

2. The system of claim 1, wherein the UV light sources emit UVC rays with a wavelength ranging from 200 to 280 nm and UVA rays with a wavelength of approximately 405 nm, and wherein the UVA rays are visible to a bystander as a safety measure to signal UV leakage from the system.

3. The system of claim 1, wherein the UV light sources have a power of 30 to 150 W, a flux of 10 to 10,000 $\mu W/cm^2$ so as to achieve an irradiation dosage of at least 2,500 $\mu W \cdot s/cm^2$ in the chamber within several seconds to several minutes of use, and an irradiation of 200 to 3,000 mW for rapid and substantially complete disinfection of the air stream.

4. The system of claim 1, further comprising an air filtration means attached to the air convection means, wherein the air filtration means removes particulates from the air stream before or after disinfecting the air stream.

5. The system of claim 1,
wherein, based on sensory data received from the UVC sensor, the electric power supplied to the UV light sources is modulated to maintain a constant level of UVC intensity in the chamber.

6. The system of claim 5, wherein, 70% of the nominal power supply is provided to new UV light sources while, when the UVC sensor detects a 10% reduction of the intensity of UVC rays in the chamber of the air purification system after use for a period time, the system increases power supplied to the UV light sources to 80% of their nominal power supply.

7. The system of claim 5, wherein the UV light sources have a rated life of 30,000 to 50,000 hours, wherein the rated life is a period of time in which the UV light sources have an optical output of no less than 70% of the nominal power output.

8. The system of claim 1, wherein operating conditions and parameters of the UV light sources and the air convection means are adjusted by a user via the operation control subsystem.

9. The system of claim 8, wherein the operation control subsystem intelligently adjusts the operating conditions and parameters based on instructions from the user saved on a smart home control appliance or encoded in a software operable with the operation control subsystem.

10. The system of claim 1, wherein the air convection means comprises an airflow detector for detecting flow rate of air therein, wherein when the flow rate of air reaches a threshold value or a range, the airflow detector provides a signal to the operation control subsystem to adjust the power of the UV light sources.

11. The system of claim 10, wherein the power of the UV light sources is adjusted in a way to maintain a PGDE Index substantially in a range of 85% to 100%.

12. The system of claim 1, wherein the interior of the chamber has one or more reflecting surfaces made of aluminum for maximal reflection of UV rays.

13. The system of claim 1, further comprising a motion sensor for alarming a person adjacent to or present within a predetermined distance of the air purification system from possible exposure to the ultraviolet light emitted by the UV light sources due to UV light leakage.

14. The system of claim 13, wherein the motion sensor is a High Frequency Doppler (HFD) sensor.

15. An air purification system, comprising:
a housing having an inlet for receiving air, an outlet for exhausting air, and one or more utility openings, wherein an air stream is passable from the inlet to the outlet;
an air convection means in the housing, which moves the air stream through the inlet from outside into a chamber in the housing, and further moves the air stream from the chamber to outside through the outlet;
a UV light subsystem within the chamber, comprising a plurality of UV light sources configured to emit UV radiation with adjustable wavelengths to irradiate the air stream passing through the chamber; and
an operation control subsystem adapted to the utility openings on the housing, by which a user controls or adjusts the air convection means and UV light subsystem, wherein when the air purification system is in operation, the air stream moved by the air convection means enters the chamber through the inlet, is irradiated by the UV light sources of the UV light subsystem, and exits through the outlet, thereby being disinfected,
wherein the UV light subsystem comprises one or more PCBs for mounting the UV light sources in the chamber, wherein the PCBs comprise aluminum, so that heat accumulated in the chamber is efficiently dissipated, thereby lowering the operating temperature of the UV light sources and elongating the lifetime of the UV light sources,
wherein the air purification system further comprises a UVC sensor inside the chamber for detecting the intensity of UVC rays emitted by the UV light sources, and
wherein the UV light sources in the chamber comprise two UVC LED strips facing one another to ensure the most potent irradiation and disinfection while minimizing UVC leakage from the air purification system.

* * * * *